United States Patent [19]

Swanson et al.

[11] Patent Number: 5,788,645
[45] Date of Patent: Aug. 4, 1998

[54] METHOD AND APPARATUS FOR EVENT PROCESSING IN BIOLOGICAL APPLICATION

[75] Inventors: David K. Swanson, Roseville; Graydon Beatty, New Brighton; Douglas Lang, Arden Hills, all of Minn.

[73] Assignee: Cardiac Pacemakers, Inc., St. Paul, Minn.

[21] Appl. No.: 657,389

[22] Filed: Jun. 3, 1996

Related U.S. Application Data

[63] Continuation of Ser. No. 884,563, May 18, 1992, abandoned.

[51] Int. Cl.[6] ................................................. G06F 159/00
[52] U.S. Cl. .......................................... 600/516; 600/515
[58] Field of Search ................................. 395/202, 203; 705/2, 3; 600/515, 516, 128, 702, 705, 710, 712

[56] References Cited

U.S. PATENT DOCUMENTS

| | | | |
|---|---|---|---|
| 4,094,310 | 6/1978 | McEachern | 128/712 |
| 4,364,397 | 12/1982 | Citron et al. | 128/710 |
| 4,794,532 | 12/1988 | Leckband et al. | 128/710 |
| 4,803,625 | 2/1989 | Fu et al. | 364/413.03 |
| 4,815,017 | 3/1989 | DeCote, Jr. | 364/602 |
| 4,924,875 | 5/1990 | Chamoun | 128/702 |

FOREIGN PATENT DOCUMENTS

| | | |
|---|---|---|
| 0017966 | 10/1980 | European Pat. Off. . |
| 0304137 | 2/1989 | European Pat. Off. . |
| 0448196 | 9/1991 | European Pat. Off. . |
| 0540144 | 5/1993 | European Pat. Off. . |
| 0632992 | 1/1995 | European Pat. Off. . |
| 2227842 | 8/1990 | United Kingdom . |
| WO92/05836 | 6/1992 | WIPO . |
| WO92/09233 | 6/1992 | WIPO . |
| WO92/14401 | 9/1992 | WIPO . |

*Primary Examiner*—Gail O. Hayes
*Assistant Examiner*—Frantzy Poinvil
*Attorney, Agent, or Firm*—Evenson, McKeown, Edwards & Lenahan, PLLC

[57] ABSTRACT

A method and apparatus for processing biological signals on an event basis. An event low pass filter (LPF) is provided which passes variations in event features below an event cut-off value, which is analogous to the time-based cutoff frequency. An event high pass filter (HPF) is provided which passes variations in event features that are above an event-rate cutoff. An event variability detector is provided which determines the variation of a discrete variable from values at prior events. An event discriminator is provided for filtering out contributions of unrelated events that are superimposed on a discrete periodic measurement of interest. In all of these techniques, sampling of a biological signal is performed in coincidence with a biological event which does not occur at a constant frequency. In accordance with another aspect, an algorithm is provided using event-based techniques for discriminating abnormal rhythms from normal sinus rhythm on the basis of atrial rate, ventricular rate, and A-V intervals. An interval conditioning stage is provided for processing intervals of atrial beats, ventricular beats, and atrial to ventricular beats and classifying intervals for each according to an adaptive triple-bin technique. The three bins are defined as "current", "fast" and "slow" and each comprises memory space for storing the count of intervals stored into the particular bin and the average value of those intervals.

36 Claims, 7 Drawing Sheets

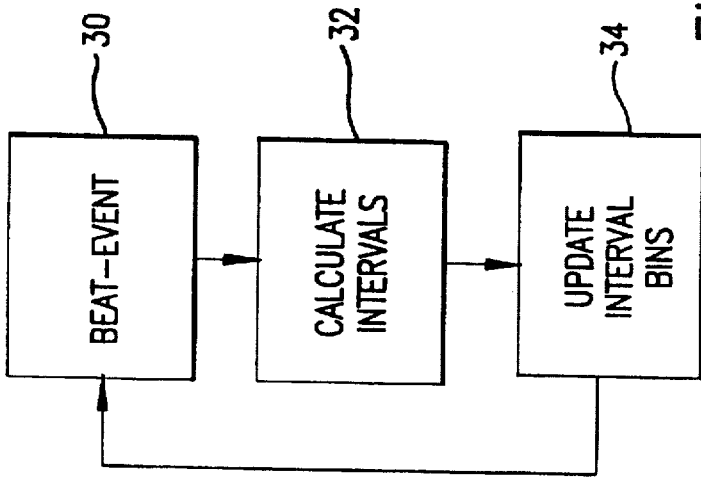

5,788,645

METHOD AND APPARATUS FOR EVENT PROCESSING IN BIOLOGICAL APPLICATION

This is a continuation application of Ser. No. 08/884,563, filed on May 18, 1992, now abandoned.

RELATED APPLICATION

This application is related to commonly assigned U.S. patent application Ser. No. 07/884,770, filed May 18, 1992, and entitled ALGORITHM FOR TACHYCARDIA DISCRIMINATION OR RATE ADAPTIVE PACING WITH MULTIPLE SENSORS now U.S. Pat. No. 5,311,874.

BACKGROUND OF THE INVENTION

The present invention relates to implantable devices and more particularly to implantable devices responsive to changes in the biological activity of the heart for treating arrhythmias of the heart.

Presently, implantable devices, such as implantable cardiac defibrillators and pacemakers, monitor the electrical and other activity of the heart. To detect an abnormal condition of the heart, these devices analyze the electrical and other cardiac signals, such as arterial pressure or cardiac volume impedance, as continuous time variables. Specifically, these systems are characterized as time-based systems which sample the cardiac signals at a constant sampling frequency and respond to changes in these signals over a characteristic period of time.

When declaring that an abnormal cardiac condition is occurring, some time-based systems compute signal characteristics such as mean and standard deviation. These parameters are determined by sampling a signal over a predetermined period of time. A disadvantage of this type of method is that only a single measurement of mean and standard deviation is made. Trends in the signal cannot be measured and examined.

Another monitoring method used in time-based systems is to measure a trend in a continuous signal by a moving window average. In this method, the signal is continuously sampled at a fixed rate. The mean is calculated using a window of consecutive samples from the sample stream. The number of samples (N) is fixed and always includes the most recent sample. At each sampling time, the most recent sample is added to the window, the oldest sample dropped and a new mean computed. This method can be thought of as a type of digital low pass filtering.

Yet another method used in time based systems is an exponential average. This method uses another type of digital low pass filter to average sampled signals. In contrast to the moving window method, this method only requires the most recent sample to compute the exponential average. While the moving window method weights all of the last N samples by 1/N, the exponential average weights only the most recent sample as 1/N, where N is analogous to a time-constant. It is possible to smooth out rapid signal fluctuations in this method by choosing an appropriate time constant. While this approach requires less memory and is easier to implement in real time than the moving window method, it has a response time that is approximately three times longer than a moving window filter of equivalent cutoff frequency.

There are several disadvantages to the time-based systems. First, nearly all time-based systems require a system clock to provide a reference for sampling the cardiac signals at a rate that is several times faster than the highest frequency component of the signal. Second, because large numbers of samples of signals must be examined over periods of time, large memories are required. In the context of implantable devices, where size and power requirements are to be minimized, large memories place severe limitations on implanting the device subcutaneously. Finally, it is difficult to separate particular key cardiac signal features from other non-cardiac signals.

SUMMARY OF THE INVENTION

It is a primary object of the present invention to provide a method and system for processing biological events, such as electrical and other cardiac signals, by modification of standard digital signal processing techniques.

It is an additional object of the present invention to provide a method and system having a decreased response time by analyzing non-constant biological events using modified digital signal processing techniques.

In accordance with the present invention, several techniques are disclosed for processing biological signals on an event basis. First, an event low pass filter (LPF) is provided which passes variations in events below an event cut-off value, which is analogous to the time-based cutoff frequency. Second, an event high pass filter (HPF) is provided which cuts off event features that are below an event-rate cutoff. Third, an event variability detector is provided which determines the variation of a discrete variable from values at prior events. Finally, an event discriminator is provided for filtering out contributions of unrelated events that are superimposed on a discrete periodic measurement of interest. In all of these techniques, sampling of a biological signal is performed in coincidence with a biological event which does not occur at a constant frequency.

In accordance with another aspect of the present invention, an algorithm is provided using event-based techniques for discriminating abnormal rhythms from normal sinus rhythm on the basis of atrial rate, ventricular rate, and A-V intervals. The algorithm centers around a stage for processing intervals of atrial beats, ventricular beats, and atrial to ventricular beats and classifying intervals for each according to an adaptive triple-bin technique. The three bins are defined as "current", "fast" and "slow" and each comprises memory space for storing the count of intervals stored into the particular bin and the average value of those intervals. A new sample of data occurs at each ventricular beat, which is defined as the event. The binned intervals are averaged by a recursive low pass filter called an exponential filter. The exponential filter operates in the event-domain rather than the time-domain.

Based on data processed during the interval condition stage, a decision logic stage determines the type of cardiac rhythm that is occurring.

The above and other objects and advantages of the present invention will become more readily apparent when reference is made to the following description taken in conjunction with the accompanying drawings.

BRIEF DESCRIPTION OF THE DRAWINGS

FIG. 5 is a flow chart diagram illustrating the fundamental procedure of a step of the algorithm shown in FIG. 4.

FIG. 6 is a diagram illustrating the arrangement of the event counters and memory cells (bins) used for storing time interval data in accordance the event-based tachyarrhythmia detection algorithm illustrated in FIG. 4.

DETAILED DESCRIPTION OF THE DRAWINGS

Figure 1:
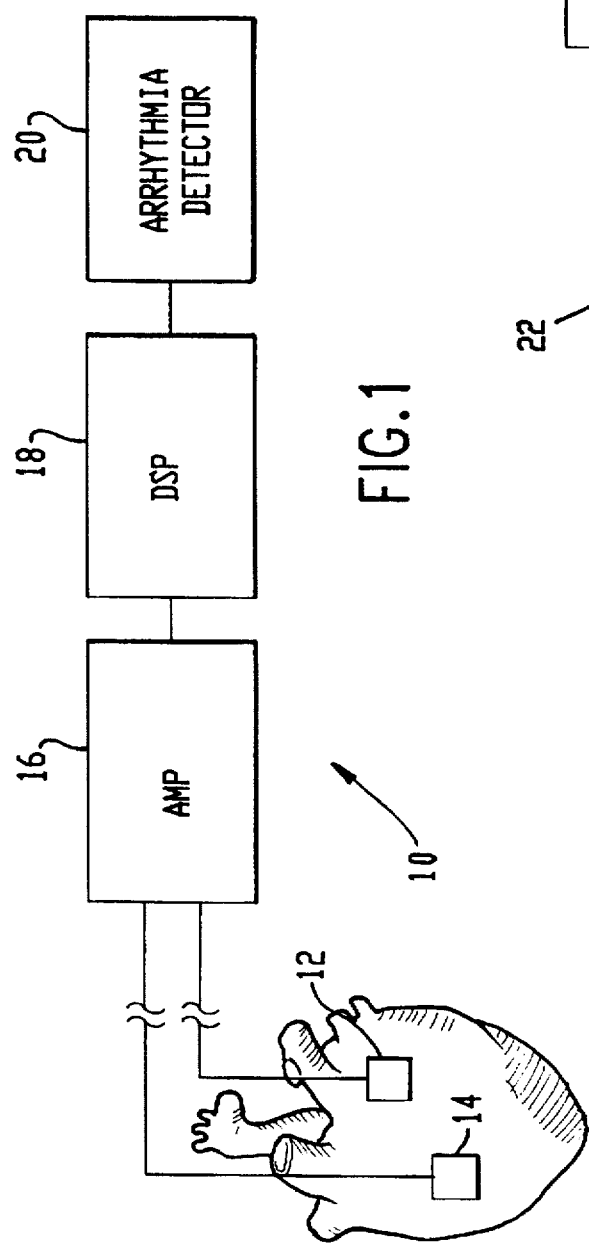
FIG. 1 is a block diagram illustrating the use of event processing in an implantable cardiac treatment system.

Referring first to FIG. 1, an implantable cardiac treatment system is generally shown at 10. The system 10 includes a plurality of cardiac sensing electrodes 12 and 14 (only two of which are shown) placed in or about the heart for sensing cardiac activity. Specifically, these sensing electrodes may provide one or more features extracted from the following signals during each cardiac event: ventricular flow, ventricular pressure, ventricular volume, cardiac electrogram, cardiac electrogram gradient, or arterial blood flow. The time at which events occur, as defined by these variables varies.

The sensing electrodes 12 and 14 are connected to an amplifier 16 which amplifies the signals picked up by the electrodes. The amplified signals are fed to a digital signal processor (DSP) 18 which analyzes and processes these signals using digital signal processing techniques described in more detail hereinafter. The DSP 18 is connected to an arrhythmia detector 20 which determined the existence of cardiac abnormalities based upon the analysis performed by the DSP 18.

Figure 2:
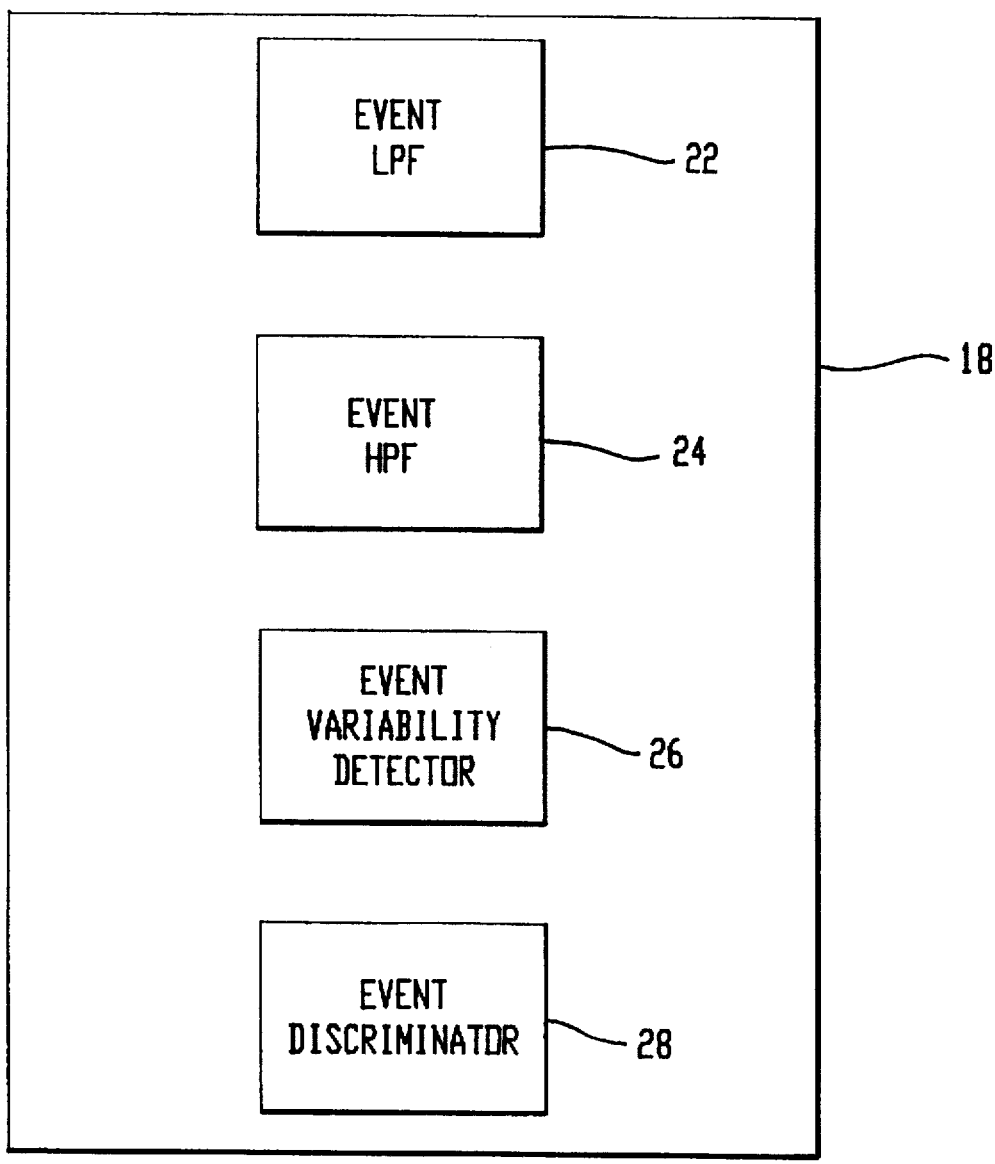
FIG. 2 is a block diagram of a digital signal processor used in an event processing algorithm according to the present invention.

The DSP 18 is shown in greater detail in FIG. 2. Specifically, the DSP 18 includes an event low pass filter 22, an event high pass filter 24, an event variability detector 26 and an event discriminator 28.

Figure 3:
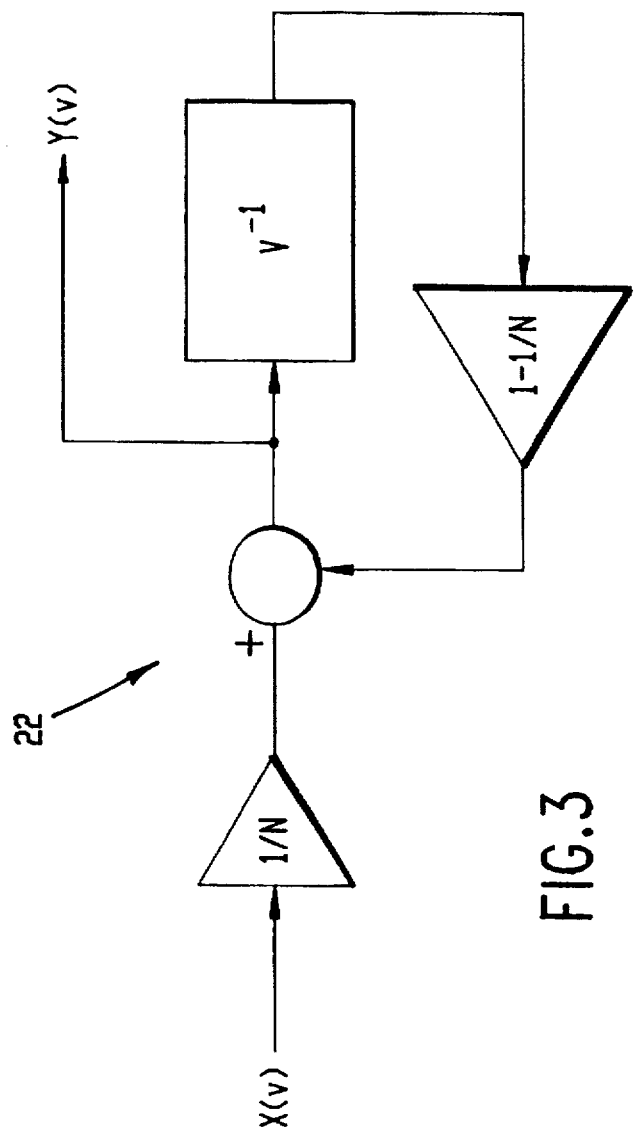
FIG. 3 is a block diagram of an event low pass filter according to the present invention.

The event low pass filter 22 is illustrated in detail in FIG. 3. A new transform operator V is defined for implementing the event low pass filter 22. This transform operator represents one event-delay which is analogous to the sample time delay in the Z transform but is designed for use for sampling parameters with variable periodicity. Analogous analytic techniques used in the Z transform may be applied in the V transform. An event average, $D_{AVE}(n)$ is defined in terms of the discrete variable $D(n)$ according to the equation:

$$D_{AVG}(n) = [1-(1/N)]D_{AVG}(n-1)+(1/N)D(n),$$

where n is an integer which represents the nth event in a sequence of events in D, $D_{AVG}(n)$ is the most recent event average of the discrete variable D, $D_{AVG}(n-1)$ is the previous event average of the discrete variable D, and D(n) is the most recent value of the discrete variable D. N is an integer representing the number of events over which the average is determined and is preset to specify the sensitivity of the event average to new values of the discrete variable D(n).

The signal flow diagram shown in FIG. 3 represents the relationship between an input event X as a function of the event transform variable v, and an output event Y also as a function of the event transform variable v. As shown, the relationship between Y(v) and X(v) is as follows:

$$Y(v) = [1/N]X(v) + [1-1/N]Y(v)v^{-1}.$$

The rate at which $D_{AVG}(n)$ changes in response to a change in the discrete variable D(n) is not specified in time. Rather, the rate at which the event average changes is specified in the number of future events to be detected. A parameter which characterizes this filter is an event constant, rather than a time constant which characterizes a time based filter. For the low pass filter shown in FIG. 3, the event constant is N−0.5. Consequently, approximately N events must occur for $D_{AVG}(n)$ to reflect 63% (1−1/e) of a step change in D(n). The event filter has a characteristic event-rate cutoff that is analogous to the time-based cutoff frequency. The event-rate cutoff is defined as:

$$ER_\infty = 1/(2\ PI(N-0.5)).$$

Variations in event features that are below the event-rate cutoff are passed unaltered while variations above the cutoff are attenuated. Variations that are equal to the event-rate cutoff are attenuated by 3dB. In a typical application, if N is set at 10, the event average of the filter may be expressed by:

$$D_{AVG}(n) = 0.9D_{AVG}(n-1) + 0.1D(n).$$

As evidenced from the above equations, the event-based filter is not dependent on a constant sampling frequency and is thus independent of time. As a result, the transient response of the event-based average is not equal to that of a time-based average. Furthermore, the event-based algorithm requires much less sampling than a time-based system. For example, one sample per heart beat is acquired by an event-based algorithm as compared to many samples per heart beat in a time-based system. Further, an event low pass filter as described above responds more quickly to events occurring at a faster rate because the response rate is inversely proportional to the rate of event sampling.

The event high pass filter 24 is used to focus on recent fluctuations of a discrete variable by eliminating baseline changes. The event high pass filter 24 is related to the event low pass filter and is defined by:

$$D_{HP}(n) = D(n) - D_{AVG}(n-1),$$

where $D_{AVG}(n-1)$ is the same as that used in the event low pass filter. The event-rate cutoff is defined the same for the event high pass filter as for the event low pass filter, but the form of the roll-off is the opposite. For the high pass filter, variations in event features that are below the event-rate cutoff are attenuated while variations above the cutoff are passes unaltered.

The event variability detector 26 determines the variation of a discrete variable $D_K$ from values at prior events $(V_k)$. The variability $V_k$ is related to the event high pass filter and is defined by:

$$V_K(n) = |D(n) - D_{AVG}(n-1)|,$$

where the right side of the equation is recognized as the absolute value of the event high pass filter. Thus, if no change in D(n) occurred, the value of the variability $V_K(n)$ is zero. Furthermore, the sensitivity of the variability detector is directly proportional to the event constant. For example, a large event-constant provides a low event-rate cutoff, yielding a detector with high sensitivity in which small event variations are sensed. As the event constant decreases, the event-rate cutoff increases and only the more highly variable event features are passed.

The event discriminator 28 is used to filter out contributions of unrelated events that are superimposed on the discrete periodic measurement of interest. Sampling occurs at the variable periodicity of the phenomenon of interest, such as the R-wave of the ECG. Periodic processes that are not correlated to the phenomenon of interest but sampled at this event frequency will vary in magnitude. The contributions of these non-correlated periodic processes can be cancelled out by an event low pass filter, leaving the information of the event or discrete variable of interest. Furthermore, the impact of these unrelated events on the discrete variability of interest can be assessed by the event variability detector.

Examples of cardiac parameters which are amenable to event discrimination include the difference in signal amplitudes at preset time intervals before and after the R-wave; the amplitude of a hemodynamic signal during the R-wave; and the peak value of a hemodynamic signal in a preset time interval after the R-wave.

FIGS. 4–9B relate to one example of the use of event processing techniques, and particularly to an algorithm for discriminating ventricular tachycardia (VT) and sinus tachycardia/supraventricular tachycardia (SVT) from normal sinus rhythm (NSR) using event-based processing techniques. Processing includes beat-by-beat updating of interval classifications and averages to provide adaptability to electrophysiologic variation in the ambulatory setting. The algorithm is based on A-rate, V-rate and A-V interval data as the discriminatory features.

Figure 4:
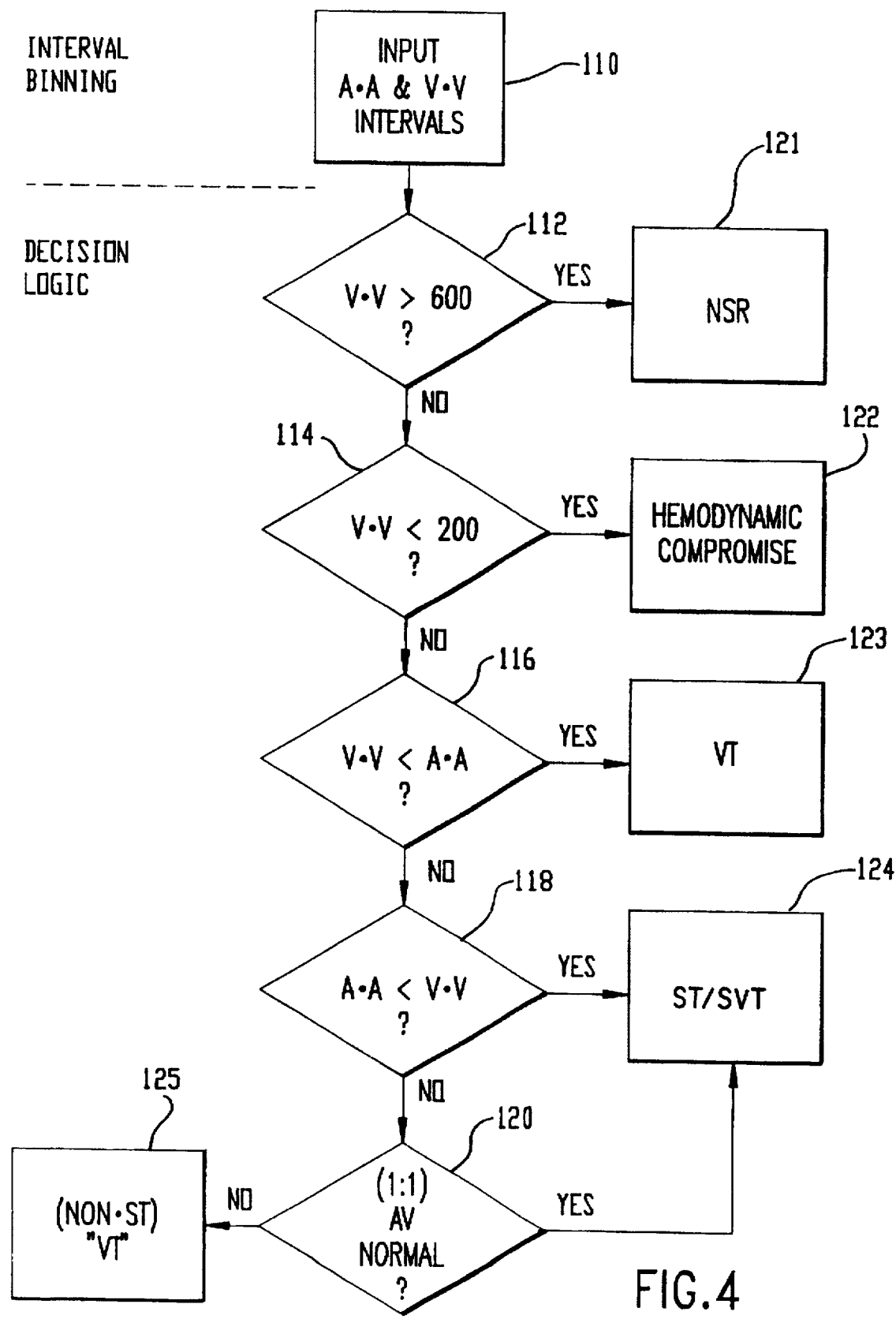
FIG. 4 is a flow chart diagram generally illustrating steps of an event-based tachyarrhythmia detection algorithm according to the present invention.

The algorithm is generally illustrated in FIG. 4 and comprises an interval binning stage and a decision logic stage. In the interval binning stage, atrial and ventricular beat data is input in step 10 to determine A-A intervals (A-rate), V-V intervals (V-rate) and A-V intervals. As will become more apparent hereinafter, step 10 conditions inter-beat intervals to provide aberrancy filtering and a therapy counter. Steps 12–20 involve decision criteria for declaring the type of cardiac rhythm on the basis of the interval conditioning (binning) procedure.

The interval binning procedure comprises, in general, three steps, as shown in FIG. 5. The first, at step 30, is to sample cardiac data at each beat event. The time intervals between consecutive atrial beats, consecutive ventricular beats, and between an atrial beat and the next ventricular beat, are calculated in step 32. This time interval data is compared with data from the previous sample or event and is used to update stored data, as shown at step 34.

Time interval data is stored according to an adaptive triple-bin technique for classifying the new time interval data, while avoiding the limitations of a simple running average. Referring to FIG. 6, three bins are defined: 1) "current"; 2) "fast"; and 3) "slow". The term "current" refers to the most prevalent interval value that occurs in the last 15 beats; the term "fast" refers to recent intervals that are much shorter than the "current" interval; and the term "slow" refers to recent intervals which are much longer than the "current" value. The "slow" and "fast" bins are hereinafter referred to as the "outlier" bins. Each bin comprises two memory spaces for storing 1) the count of intervals that have been sorted into the bin, and 2) the average value of all of the intervals sorted into the bin. In the present implementation, the count data is 4 bits wide and the average value is 16 bits wide. Three triple-bin arrays are provided, one each for ventricular, atrial and A-V intervals.

Figure 7:
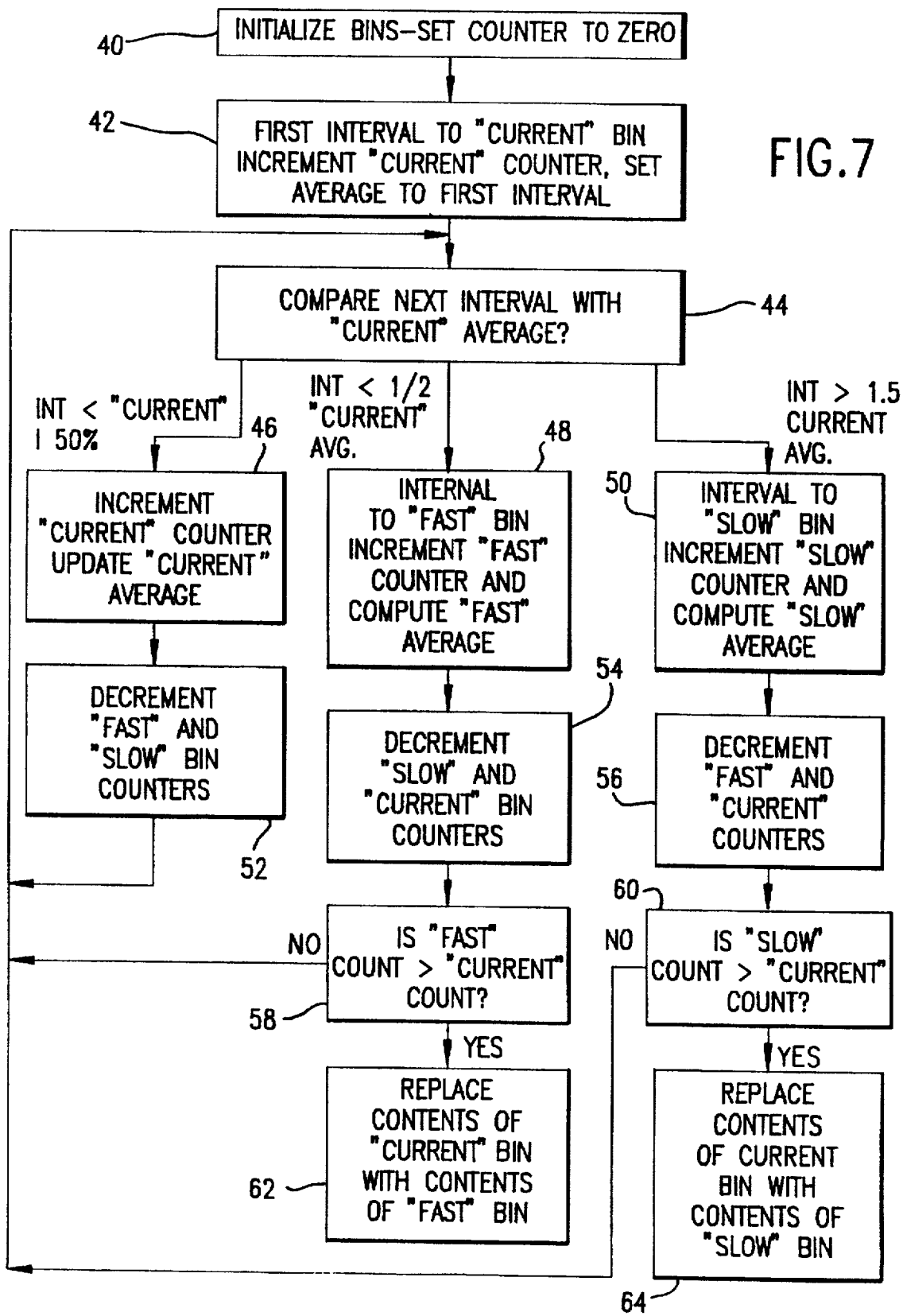
FIG. 7 is a flow diagram illustrating the steps of storing time interval data in bins according to the algorithm illustrated in FIG. 4.

FIG. 7 illustrates the procedure for classifying or sorting time interval data into the bins. The procedure applies to the ventricular interval data, atrial interval data and A-V interval data, which is implemented simultaneously in each of the three triple-bin arrays.

First, in step 40, the bins are initialized by setting all bin-counts to zero. A count of zero implies that there is no history of sorted intervals on which to base calculation of an average interval. Bin averages are never set to zero because this would imply an infinite heart rate.

Once sensing has begun, in step 42, the first interval is assigned to the "current" bin, the count of the "current" bin is incremented to one, and the initial average of the "current" bin is set to the first interval value.

The next time interval is compared with the "current" average in step 44. If the next interval is within plus or minus 50% of the "current" average, it is declared that this interval fits into the "current" bin. This percentage range defines the width of the bin and is intended to be a programmable parameter. The plus and minus percentages need not be programmed to the same value. The count of the "current" bin is incremented by one in step 46 and the "current" bin average is updated on the basis of the new time interval value. All intervals that fit into the "current" bin are averaged to compute a new "current" average; however, the bin count can never exceed 15.

Intervals subsequent to the first interval that are less than one-half (or other programmed value) the "current" average are declared a "fast" outlier. The first "fast" interval initializes the "fast" bin average in step 48, in the same way that the "current" bin average is initialized. Similarly, intervals subsequent the first interval that are greater than 1.5 times (or other programmed value) the "current" average are declared a "slow" outlier and are stored in the "slow" bin in step 50.

Each time any bin count is incremented, the other two bin counts are decremented each by one count. The averages in those bins are left unchanged. This is shown in steps 52, 54 and 56.

Sustained changes in rate cause recurrent increments in an outlier bin while decrementing the "current" bin (as well as the other outlier bin). The bin count in each outlier bin is compared with the count in the "current" bin, in steps 58 and 60. If the bin count in either outlier bin exceeds the bin count in the "current" bin, the contents of that outlier bin replaces the contents of the "current" bin, as shown at steps 62 and 64.

Only average values from each of the "current" bins are passed to the decision logic stage of the algorithm. Thus, values in the outlier bins reach the decision logic section only when they replace the contents of the "current" bin.

Certain features are "built-in" to the interval conditioning stage of the algorithm. First, steps 48 and 50 provide an aberrancy filtering effect. Second, steps 52–64 provide the ability to adapt to abrupt changes in rate within 9 beats. Moreover, the width of the "current" bins, defined as a plus-and-minus percentage of the most recent average value, provides adaptability to normal physiologic variability. In this way, the absolute variation in cycle length that fits the "current" bin is allowed to be wider for normal sinus rhythm than for faster rhythms.

Furthermore, the action of incrementing and decrementing the bin counts serves as a therapy counter. For example, a sustained normal rhythm will hold the "current" bin count at 15 and the outlier bin counts at zero. If the rhythm breaks into a fast VT, the "fast" bin will gradually increment while the "current" bin will gradually decrement. In 9 beats, the outlier bin count will exceed and overtake the "current" bin. Thus, VT is declared in 9 beats.

Critical to the operation of the algorithm is the use of event-based processing. Each event is defined by the occurrence of a ventricular beat. The A-V interval is calculated as the time difference between the occurrence of a ventricular beat and the previous atrial beat. Consequently, the A-V interval can never be negative. Every occurrence of a ventricular beat prompts the interval update process of binning and averaging according to the procedure shown in FIG. 7.

If the atrial rate is faster than the ventricular rate, there will be several occurrences of atrial beats within the latest V-V interval. All of the atrial events will be tallied and averaged up to, but not beyond that of the ventricular event. However, this will not compromise the analysis of A-V intervals since they are used for arrhythmia classification only when the A-A interval equals the V-V interval.

If the ventricular rate is faster than the atrial rate, there will be no occurrences of atrial events over several V-V intervals. In this case, the last saved A-A and A-V average values will remain unchanged until a new atrial beat occurs several beats later to update the A-A and A-V average values. During the intervening multiple ventricular events, the decision logic will compare each updated V-V average with the unchanged A-A average. The average A-V value will be ignored since it is used only when A-A equals V-V. If the atrial rate is equal to the ventricular rate, there will be an occurrence of A for every V, producing an update of A-A, V-V and A-V average values at every occurrence of V.

The binned intervals are averaged by a recursive low pass filter called an "exponential filter", similar to that shown in FIG. 3. The recursive filter is very memory efficient since each incoming interval is scaled and added to the previous result. The filter is operating in the event-domain rather than the time-domain. As explained in the foregoing, samples in the event-domain are not necessarily evenly spaced in time, while samples in the time-domain are absolutely evenly spaced in time. While the primary purpose of averaging is to filter out spurious data, it also provides another level of adaptability to normal physiologic trends within each adaptive bin.

The exponential event filter is defined as:

$$AVE_n = \frac{IVAL_n + (EC - 1)AVE_{n-1}}{EC}$$

where, $AVE_n$ is the average value for the present beat event; $AVE_{n-1}$ is the average value for the previous beat event; $IVAL_n$ is the incoming present interval to be averaged; and EC is the event constant (which is analogous to a time constant in the time domain).

Figure 8:
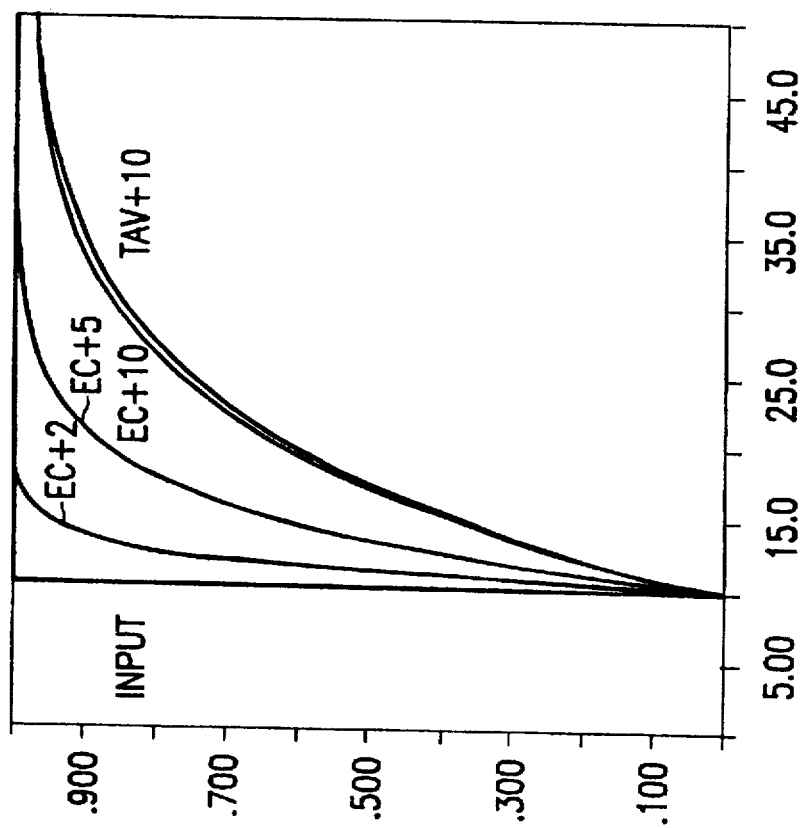
FIG. 8 is a graphical illustration of the characteristics of an event low pass filter used to compute the average time intervals according to the algorithm illustrated in FIG. 4.

FIG. 8 illustrates the response of the exponential event low pass filter to a step input with event constants of 2, 5, and 10. As a reference, the exact exponential is shown with EC=10. As is apparent from this figure, this filter performs like a standard first-order filter. It has been found that implementing the filter with an event constant of 5, optimizes the opposing characteristics of both response time and smoothing. Substituting the value 5 for EC into the above equation simplifies the expression:

$$AVE_n = \tfrac{1}{5}(IVAL_n) + \tfrac{4}{5}(AVE_{n-1}).$$

Hence, the updated average is created by adding a small portion of the incoming interval to a large portion of the previous average.

Figure 9A:
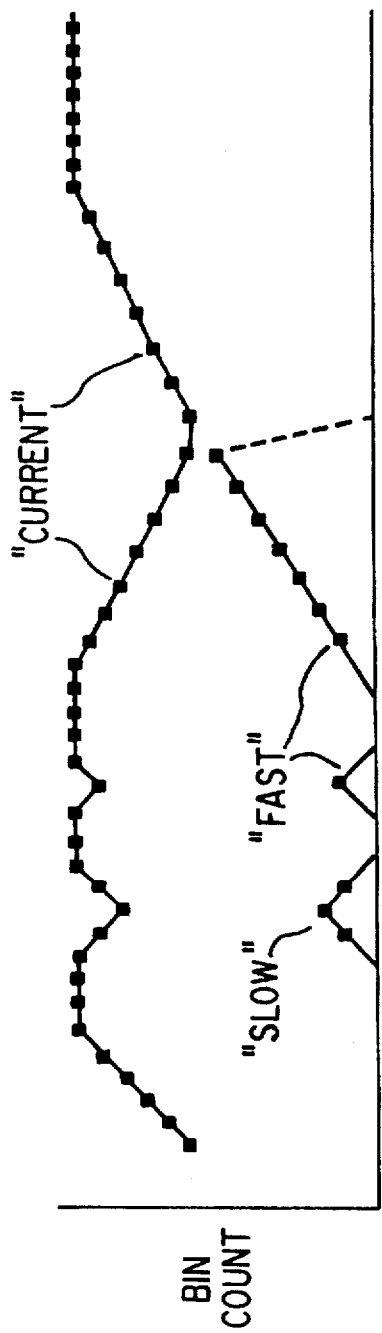
FIGS. 9A and 9B are graphical illustrations of bincount history and cardiac rhythm history.
Figure 9B:
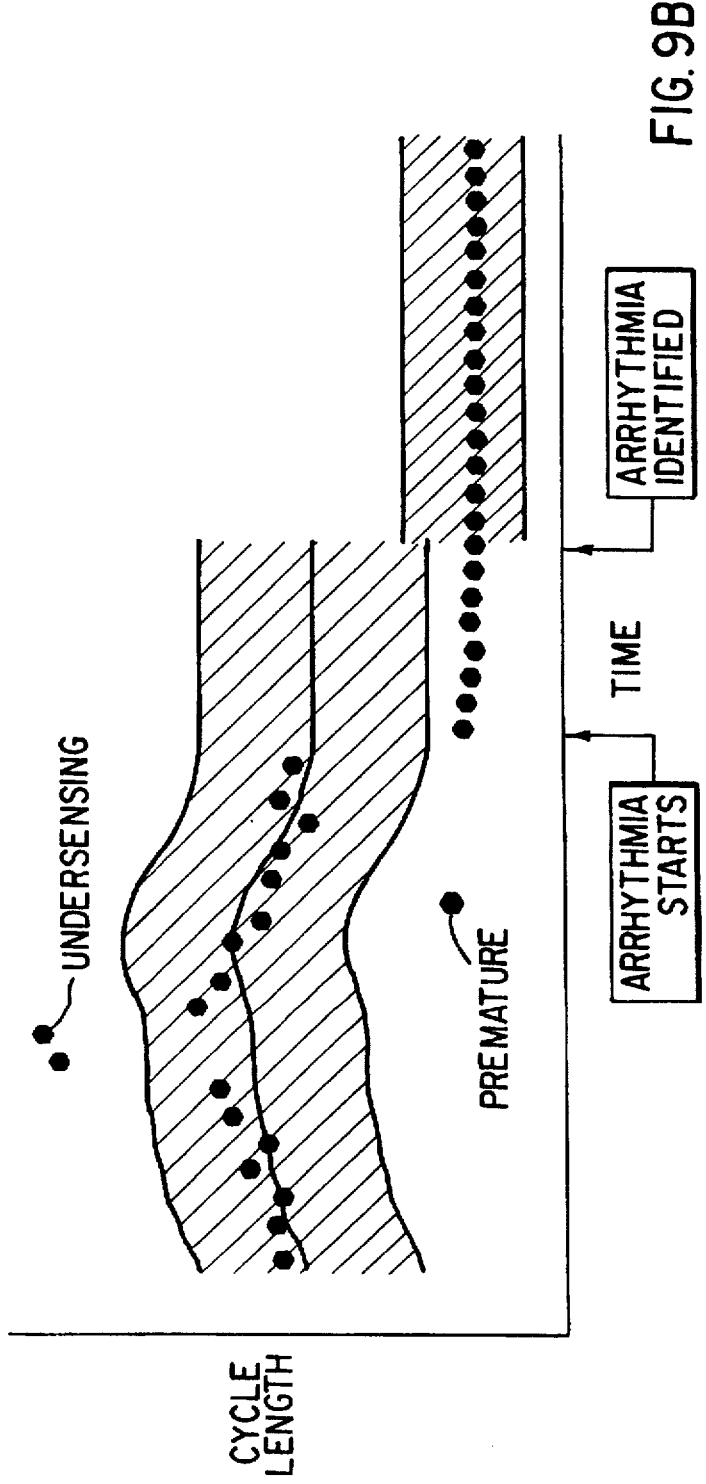

FIGS. 9A and 9B illustrate an example of the entire interval processing method. In FIG. 9B, the plot of asterisks illustrates a respiration-modulated normal rhythm that breaks into a fast rhythm. During normal rhythm, there are two missed detections and subsequently a fast premature beat. The shaded region depicts the width of the "current" bin. FIG. 9A shows the operation of the bin-counts responding to the cardiac activity of FIG. 9B. The plot of asterisks show the bin-counts for the "current", "slow" and "fast" bins. Importantly, the "fast" bin overtakes the current bin in nine beats at the point labelled "arrhythmia identified" in FIG. 9B.

Referring to FIG. 4 again, the decision logic stage will be described. This portion of the algorithm is designed as a hierarchical decision logic tree for classifying bin-averaged intervals according to rhythm on a beat-by-beat basis. Both rate and timing criteria are built into the logic tree.

At step 12, the normal rate-zone is established according to ventricular-rate criteria. V-V intervals that are longer than 600 ms (slower than 100 bpm) are declared NSR. In step 14, V-V intervals that are shorter than 280 ms (faster than 214 bpm) are declared VT with assumed hemodynamic compromise.

The three remaining decision steps, 16, 18 and 20, establish the middle rate-zones (rates between 100 and 214 bpm) according to ventricular rate, atrial rate and A-V timing criteria. In step 16, V-V intervals that are shorter than A-A intervals by 10% or less are declared VT by the ventricular criterion: ventricular rate is faster than atrial rate. Conversely, V-V intervals that are longer than A-A intervals by 10% or more are declared ST/SVT by the atrial criterion in step 18. Finally, V-V and A-A intervals that are within 10% of each other are assumed to represent 1:1 conduction. Such cases are analyzed in decision step 20 by comparing the "current" A-V interval to the long-term average A-V interval during NSR. This long-term average is determined by continually updating a separate exponential average of the binned A-V intervals from only those beats that were classified as NSR in step 12.

This separate exponential event filter has a long event constant of 4096, providing an automatic and adaptive determination of average A-V over approximately a five-hour window of NSR. A-V intervals that are within −25% and +10% (or other programmed value) of average A-V at NSR are declared ST/SVT by the ST criterion. This is based on the tendency for A-V intervals to shorten slightly during exercise induced ST. By contrast, A-V intervals during VT tend to lengthen. A-V intervals that fall outside the "normal" ranged defined in the foregoing are declared VT by failing the ST criterion.

An important advantage of the algorithm according to the present invention is its adaptability. The bin limits, interval averages, and A-V value for normal sinus rhythm, provide for automatic tracking of large changes in rhythm and adjust to small physiologic variations to maximize specificity and sensitivity for differentiating VT and ST from normal sinus rhythm.

The algorithm may be enhanced by separating the ST classification from the combined ST/SVT classification, allowing for graded therapy for SVT and no therapy for ST. An interval variability measure may be added to measure rate of onset of arrhythmias, to differentiate polymorphic VT from monomorphic VT, to confirm the need to deliver therapy and to detect atrial fibrillation.

The above description is intended by way of example only and is not intended to limit the present invention in any way except as set forth in the following claims.

We claim:

1. A method for sensing biological parameters to evaluate a cardiac rhythm comprising the steps of:

sensing a biological parameter at a non-constant frequency associated with a naturally occurring biological event;

converting said biological parameter to corresponding signals;

utilizing said signals to determine an abnormal condition in said naturally occurring biological event by:

determining atrial interval values, ventricular interval values and atrial-ventricular interval values; and comparing said atrial interval values, said ventricular interval values and said atrial-ventricular interval values with stored data from a previous event, thereby evaluating the cardiac rhythm.

2. A method for sensing and processing biological parameters related to cardiac activity for determining cardiac abnormalities comprising the steps of:

sensing a biological parameter related to cardiac activity at a non-constant frequency coincident with a naturally occurring biological event;

converting said biological parameter to corresponding signals;

determining values of the biological parameter from said signals;

low pass filtering the values of the biological parameter by computing a running average of a value of said biological parameter at each biological event comprising the step of adding a fraction of a value of said biological parameter at a current event to an average of all prior values of said biological parameter calculated at an immediately preceding biological event;

transmitting said values to an arrhythmia detector; and determining atrial interval values, ventricular interval values and atrial-ventricular interval values; and determining cardiac abnormalities by comparing said atrial interval values, said ventricular interval values and said atrial-ventricular integral values with stored data from a previous event.

3. The method of claim 2, wherein said biological event is a ventricular beat.

4. The method of claim 3, wherein said biological parameter is the time interval between consecutive heart beats.

5. The method of claim 3, wherein said biological parameter is the time interval between consecutive atrial beats.

6. The method of claim 3, wherein said biological parameter is the time interval between an atrial beat and the next ventricular beat.

7. The method of claim 2, and further comprising the step of high pass filtering on an event basis the values of the biological parameters by subtracting from the current value of said biological parameter the low pass average computed at the immediately preceding event.

8. The method of claim 7, and further comprising the step of determining the variation of the value of said biological parameter at a current event from values at preceding biological events by determining the absolute value of the high pass filtered value of the biological parameter.

9. A method for sensing and processing values of a biological parameter for determining cardiac abnormalities comprising the steps of:

sensing a biological parameter related to cardiac activity at a non-constant frequency coincident with a naturally occurring biological event;

converting said biological parameter to corresponding signals;

low pass filtering values of said biological parameter by passing unaltered, variations in values of said biological parameter that are below an event-rate cutoff and attenuating variations in values of said biological parameter that are above the event-rate cutoff;

transmitting said values to an arrhythmia detector; and determining atrial interval values, ventricular interval values and atrial-ventricular interval values; and determining cardiac abnormalities by comparing said atrial interval values, said ventricular interval values and said atrial-ventricular interval values with stored data from a previous event.

10. A method for sensing and processing values of a biological parameter for detecting cardiac abnormalities comprising the steps of:

sensing a biological parameter related to cardiac activity at a non-constant frequency coincident with a naturally occurring biological event;

converting said biological parameter to corresponding signals;

determining values of the biological parameter from said signals;

high pass filtering values of said biological parameter by passing unaltered, variations in values of said biological parameter that are above an event-rate cutoff and attenuating variations in values of said biological parameter that are below the event-rate cutoff;

transmitting said values to an arrhythmia detector; and determining atrial interval values, ventricular interval values and atrial-ventricular interval values; and detecting cardiac abnormalities by comparing said atrial interval values, said ventricular interval values and said atrial-ventricular interval values with stored data from a previous event.

11. A method for detecting an abnormal cardiac rhythm comprising the steps of:

sensing atrial and ventricular activity of the heart;

converting said activity to signals corresponding to atrial (A) beats;

converting said activity to signals corresponding to ventricular (V) beats;

computing at the occurrence of each ventricular beat the time interval between consecutive atrial beats, consecutive ventricular beats and the A-V time interval;

continuously computing at the occurrence of each ventricular beat the average of the time interval between consecutive atrial beats, consecutive ventricular beats and the A-V time interval;

comparing the time interval between consecutive atrial beats, consecutive ventricular beats and the A-V time intervals, computed at the current ventricular beat with the average computed at the immediately preceding ventricular beat;

providing first, second and third memory locations for each of the time intervals of atrial beats and ventricular beats and A-V time intervals;

storing the average of the time intervals of the atrial beats, ventricular beats and A-V time intervals at the current ventricular beat in the respective first memory location dedicated to time intervals which are a predetermined amount of the average at the immediately preceding ventricular beat and incrementing a count of the number of time intervals stored to said first memory location;

storing the average of the time intervals of the atrial beats, ventricular beats and A-V time intervals at the current ventricular beat in the respective second memory location dedicated to time intervals stored to said first memory location and incrementing a count of the number of time intervals stored to said second memory location;

storing the average of the atrial beats, ventricular beats and A-V time intervals at the current ventricular beat in the respective third memory location dedicated to time intervals which differ from the average at the immediately preceding ventricular beat less than said predetermined amount and incrementing a count of the number of time intervals stored to said third memory location;

comparing the counts of the second and third memory locations of the respective atrial beats, ventricular beats, and A-V time intervals, with the count of the first memory location at each ventricular beat;

replacing the contents of the first memory location with the contents of the second memory location of the respective atrial beats, ventricular beats and A-V time intervals, if the count of time intervals stored to said second memory location exceeds the count of time intervals stored to said first memory location;

replacing the contents of the first memory location with the contents of the third memory location of the respective atrial beats, ventricular beats and A-V time intervals, if the count of time intervals stored to said third memory location exceeds the count of time intervals stored to said first memory location;

examining the contents of said first memory location of the respective atrial beats, ventricular beats and A-V time interval, at each ventricular beat; and detecting an abnormal cardiac rhythm based on the average of the contents of the first memory location and by comparing atrial beats, ventricular beats and A-V time intervals with stored data from a previous event.

12. The method of claim 11, and further comprising the steps of:

decrementing the count of time intervals stored to said second and third memory locations each time the count of time intervals stored to said first memory location is incremented;

decrementing the count of time intervals stored to said first and third memory locations each time the count of time intervals stored to said second memory location is incremented; and decrementing the count of time intervals stored to said first and second memory locations each time the count of time intervals stored to said third memory location is incremented.

13. The method of claim 11, wherein said step of determining the type of cardiac rhythm comprises the step of declaring that the cardiac rhythm is normal sinus rhythm if the content of the first memory location for ventricular beats is greater than a first predetermined threshold.

14. The method of claim 11, wherein said step of determining the type of cardiac rhythm comprises the step of declaring that the cardiac rhythm is ventricular tachycardia with hemodynamic compromise if the content of the first memory location for ventricular beats is less than a second predetermined threshold and not greater than a first predetermined threshold.

15. The method of claim 11, wherein said step of determining the type of cardiac rhythm comprises the step of declaring that the cardiac rhythm is ventricular tachycardia if the content of the first memory location for atrial time intervals is greater than the content of the first memory location of ventricular beats and the content of the first memory location for ventricular beats is not greater than a first predetermined threshold.

16. The method of claim 11, wherein said step of determining the type of cardiac rhythm comprises the step of declaring that the cardiac rhythm is supraventricular tachycardia or sinus tachycardia if the content of the first memory location for atrial time intervals is less than the content of the first memory location for ventricular beats and the content of the first memory location for ventricular beats is not greater than a first predetermined threshold and not less than a second predetermined threshold.

17. The method of claim 11, wherein said step of determining the type of cardiac rhythm comprises the step of declaring that the cardiac rhythm is supraventricular tachycardia or sinus tachycardia if the atrial interval value is within a programmed percentage boundary above and below the ventricular interval value and if the content of the first memory location for A-V time intervals is within a programmed first percentage above and second percentage below a long-term exponential average of A-V intervals measured during normal sinus rhythm.

18. The method of claim 11, wherein said step of determining the type of cardiac rhythm comprises the step of declaring that the cardiac rhythm is ventricular tachycardia if the atrial interval value is within a programmed percentage boundary above and below the ventricular interval value and if the content of the first memory location for A-V time intervals is not within a programmed first percentage above and second percentage below a long-term exponential average of A-V intervals measured during normal sinus rhythm.

19. An apparatus for sensing biological parameters to evaluate a cardiac rhythm comprising:

sensing electrodes for sensing a biological parameter at a non-constant frequency associated with a naturally occurring biological event;

an amplifier connected to said sensing electrodes for amplifying and developing a signal corresponding with said biological parameter; and a digital signal processor connected to said amplifier for analyzing and processing said signal to determine an abnormal condition in said naturally occurring biological event including means for determining atrial internal values and ventricular interval values; and an arrhythmia detector included in said digital signal processor for determining an abnormal condition by comparing the atrial interval values and ventricular interval values, whereby the cardiac rhythm is evaluated.

20. An apparatus for sensing and processing biological parameters related to cardiac activity for determining cardiac abnormalities comprising:

sensing electrodes for sensing a biological parameter related to cardiac activity at a non-constant frequency coincident with a naturally occurring biological event and for converting said biological parameter to corresponding signals;

a digital signal processor including a low pass filter for determining values of the biological parameter from said signals;

said low pass filter for filtering the values of the biological parameter by computing a running average of a value of said biological parameter at each biological event comprising means for adding a fraction of a value of said biological parameter at a current event to an average of all prior values of said biological parameter calculated at an immediately preceding biological event; and an arrhythmia detector connected to said digital signal processor for determining cardiac abnormalities by comparing obtained atrial interval values, ventricular interval values and atrial-ventricular interval values obtained from said processor with stored data from a previous event.

21. The apparatus of claim 20, wherein said biological event is a ventricular beat.

22. The apparatus of claim 21, wherein said biological parameter is the time interval between consecutive heart beats.

23. The apparatus of claim 21, wherein said biological parameter is the time interval between consecutive atrial beats.

24. The apparatus of claim 21, wherein said biological parameter is the time interval between an atrial beat and the next ventricular beat.

25. The apparatus of claim 20, and further comprising a high pass filter for filtering on an event basis the values of the biological parameter by subtracting from current values of said biological parameter a low pass average computed at the immediately preceding event.

26. The apparatus of claim 25, and further comprising means for determining the variation of the value of said biological parameter at a current event from values at preceding biological events by determining the absolute value of the high pass filtered value of the biological parameter.

27. An apparatus for sensing and processing values of a biological parameter for determining cardiac abnormalities comprising:

sensing electrodes for sensing a biological parameter related to cardiac activity at a non-constant frequency coincident with a naturally occurring biological event and for converting said biological parameter to corresponding signals;

a low pass filter for filtering values of said biological parameters by passing unaltered, variations in values of said biological parameter that are below an event-rate cutoff and attenuating variations in values of said biological parameter that are above the event-rate cutoff; and an arrhythmia detector connected to said digital signal processor for determining cardiac abnormalities by comparing obtained atrial interval values, ventricular interval values and atrial-ventricular interval values obtained from said processor with stored data from a previous event.

28. An apparatus for sensing and processing values of a biological parameter for detecting cardiac abnormalities comprising:

sensing electrodes for sensing a biological parameter related to cardiac activity at a non-constant frequency coincident with a naturally occurring biological event and for converting said biological parameter to corresponding signals;

a digital signal processor including a high pass filter for determining values of the biological parameter from said signals;

said high pass filter for filtering values of said biological parameter by passing unaltered, variations in values of said biological parameter that are above an event-rate cutoff and attenuating variations in values of said biological parameter that are below the event-rate cutoff; and an arrhythmia detector connected to said digital signal processor for determining cardiac abnormalities by comparing obtained atrial interval values, ventricular interval values and atrial-ventricular internal values obtained from said processor with store data from a previous event.

29. An apparatus for detecting an abnormal cardiac rhythm comprising:

means for sensing atrial and ventricular activity of the heart;

means for converting said activity to signals corresponding to atrial (A) beats;

means for converting said activity to signals corresponding to ventricular (V) beats;

means for computing at the occurrence of each ventricular beat an atrial interval value between consecutive atrial beats, a ventricular interval value between consecutive ventricular beats and an A-V time interval;

means for continuously computing at the occurrence of each ventricular beat the average of the time interval between consecutive atrial beats, consecutive ventricular beats and the A-V time interval;

means for comparing the time interval between consecutive atrial beats, consecutive ventricular beats and the A-V time interval, computed at the current ventricular beat with the average computed at the immediately preceding ventricular beat;

means for providing first, second and third memory locations for each of the time intervals of atrial beats and ventricular beats and A-V time intervals;

means for storing the average of the time intervals of the atrial beats, ventricular beats and A-V time intervals at the current ventricular beat in the respective first memory location dedicated to time intervals which are a predetermined amount of the average at the immediately preceding ventricular beat and incrementing a count of the number of time intervals stored to said first memory location;

means for storing the average of the time intervals of the atrial beats, ventricular beats and A-V time intervals at the current ventricular beat in the respective second memory location dedicated to time intervals stored to said first memory location and incrementing a count of the number of time intervals stored to said second memory location;

means for storing the average of the atrial beats, ventricular beats and A-V time intervals at the current ventricular beat in the respective third memory location dedicated to time intervals which differ from the average at the immediately preceding ventricular beat less than said predetermined amount and incrementing a count of the number of time intervals stored to said third memory location;

means for comparing the counts of the second and third memory locations of the respective atrial beats, ventricular beats, and A-V time intervals with the count of the first memory location at each ventricular beat;

means for replacing the contents of the first memory location with the contents of the second memory location of the respective atrial beats, ventricular beats and A-V time intervals, if the count of time intervals stored to said second memory location exceeds the count of time intervals stored to said first memory location;

means for replacing the contents of the first memory location with the contents of the third memory location of the respective atrial beats, ventricular beats and A-V time intervals, if the count of time intervals stored to said third memory location exceeds the count of time intervals stored to said first memory location;

means for examining the contents of said first memory location of the respective atrial beats, ventricular beats and A-V time interval, at each ventricular beat; and means for detecting abnormal cardiac conditions based on the average of the contents of the first memory location.

30. The apparatus of claim 29, and further comprising:

means for decrementing the count of time intervals stored to said second and third memory locations each time the count of time intervals stored to said first memory location is incremented;

means for decrementing the count of time intervals stored to said first and third memory locations each time the count of time intervals stored to said second memory location is incremented; and means for decrementing the count of time intervals stored to said first and second memory locations each time the count of time intervals stored to said third memory location is incremented.

31. The apparatus of claim 29, wherein said means for determining the type of cardiac rhythm comprises means for declaring that the cardiac rhythm is normal sinus rhythm if the content of the first memory location for ventricular beats is greater than a first predetermined threshold.

32. The method of claim 29, wherein said means for determining the type of cardiac rhythm comprises means for declaring that the cardiac rhythm is ventricular tachycardia with hemodynamic compromise if the content of the first memory location for ventricular beats is less than a second predetermined threshold and not greater than a first predetermined threshold.

33. The apparatus of claim 29, wherein said means for determining the type of cardiac rhythm comprises means for declaring that the cardiac rhythm is ventricular tachycardia if the content of the first memory location for atrial time intervals is greater than the content of the first memory location of ventricular beats and the content of the first memory location for ventricular beats is not greater than a first predetermined threshold.

34. The apparatus of claim 29, wherein said means for determining the type of cardiac rhythm comprises means for declaring that the cardiac rhythm is supraventricular tachycardia or sinus tachycardia if the content of the first memory location for atrial time intervals is less than the content of the first memory location for ventricular beats and the content of the first memory location for ventricular beats is not greater than a first predetermined threshold and not less than a second predetermined threshold.

35. The apparatus of claim 29, wherein said means for determining the type of cardiac rhythm comprises means for declaring that the cardiac rhythm is supraventricular tachycardia or sinus tachycardia if the atrial interval value is within a programmed percentage boundary above and below the ventricular interval value and if the content of the first memory location for A-V time intervals is within a programmed first percentage above and second percentage below a long-term exponential average of A-V intervals measured during normal sinus rhythm.

36. The apparatus of claim 29, wherein said means for determining the type of cardiac rhythm comprises means for declaring that the cardiac rhythm is ventricular tachycardia if the atrial interval value is within a programmed percentage boundary above and below the ventricular interval value and if the content of the first memory location for A-V time intervals is not within a programmed first percentage above and second percentage below a long-term exponential average of A-V intervals measured during normal sinus rhythm.

* * * * *